(12) United States Patent
Caballero Tapia et al.

(10) Patent No.: US 11,395,861 B2
(45) Date of Patent: Jul. 26, 2022

(54) DEVICE FOR DIFFUSING VOLATILE SUBSTANCES

(71) Applicant: ZOBELE HOLDING S.P.A., Trento (IT)

(72) Inventors: Moisés Caballero Tapia, Barcelona (ES); Jordi Masó Sabaté, Barcelona (ES); Joaquim Llorente Alonso, Barcelona (ES)

(73) Assignee: ZOBELE HOLDING SPA, Trento (IT)

( * ) Notice: Subject to any disclaimer, the term of this patent is extended or adjusted under 35 U.S.C. 154(b) by 8 days.

(21) Appl. No.: 16/308,006

(22) PCT Filed: Jun. 7, 2017

(86) PCT No.: PCT/EP2017/063801
§ 371 (c)(1),
(2) Date: Dec. 7, 2018

(87) PCT Pub. No.: WO2017/211877
PCT Pub. Date: Dec. 14, 2017

(65) Prior Publication Data
US 2020/0179555 A1 Jun. 11, 2020

(30) Foreign Application Priority Data
Jun. 8, 2016 (ES) .................................. P201630769

(51) Int. Cl.
*A61L 9/12* (2006.01)
(52) U.S. Cl.
CPC ..................................... *A61L 9/127* (2013.01)
(58) Field of Classification Search
CPC . A61L 9/127; A61L 2209/133; A61L 2209/15
See application file for complete search history.

(56) References Cited

U.S. PATENT DOCUMENTS 2,474,605 A * 6/1949 Wheeler ................... B05B 1/00
422/305
2,616,759 A 11/1952 Walsh
(Continued)

FOREIGN PATENT DOCUMENTS

EP 1 839 684 A1 10/2007
JP WO2006038323 * 4/2006 ............. A61L 9/127
(Continued)

OTHER PUBLICATIONS

International Search Report dated Oct. 27, 2017 in corresponding PCT International Application No. PCT/EP2017/063801.
(Continued)

*Primary Examiner* — Qingzhang Zhou
(74) *Attorney, Agent, or Firm* — Ostrolenk Faber LLP

(57) ABSTRACT

A device including a receptacle that defines a neck. A liquid that impregnates diffusion means is housed inside the receptacle. The diffusion means includes a flexible band and a rigid band in contact with each other, the flexible band being in contact with the liquid inside the receptacle. The device also includes an inner closing element that fits tightly inside the neck and a regulation element complementary to the inner closing element. The rigid band is associated with the regulation element, the position of which determines the surface of the rigid band arranged on the outside of the receptacle. The device facilitates accurate regulation of the exposed surface of the rigid band, thereby regulating the intensity of the perfume in a room.

12 Claims, 2 Drawing Sheets

(56) References Cited

U.S. PATENT DOCUMENTS

| | | | |
|---|---|---|---|
| 3,587,968 A | 6/1971 | Hennart et al. | |
| 4,621,768 A * | 11/1986 | Lhoste | A61L 9/127 |
| | | | 239/59 |
| 5,832,648 A * | 11/1998 | Malone | A01M 31/008 |
| | | | 239/47 |
| 2006/0016904 A1 * | 1/2006 | Caserta | A61P 9/12 |
| | | | 239/34 |
| 2008/0142613 A1 * | 6/2008 | Brown | A01M 1/2077 |
| | | | 239/47 |

FOREIGN PATENT DOCUMENTS

| | | |
|---|---|---|
| WO | WO 2006/114013 A1 | 11/2006 |
| WO | WO 2011/040590 A1 | 4/2011 |

OTHER PUBLICATIONS

Written Opinion dated Oct. 27, 2017 in corresponding PCT International Application No. PCT/EP2017/063801.

* cited by examiner

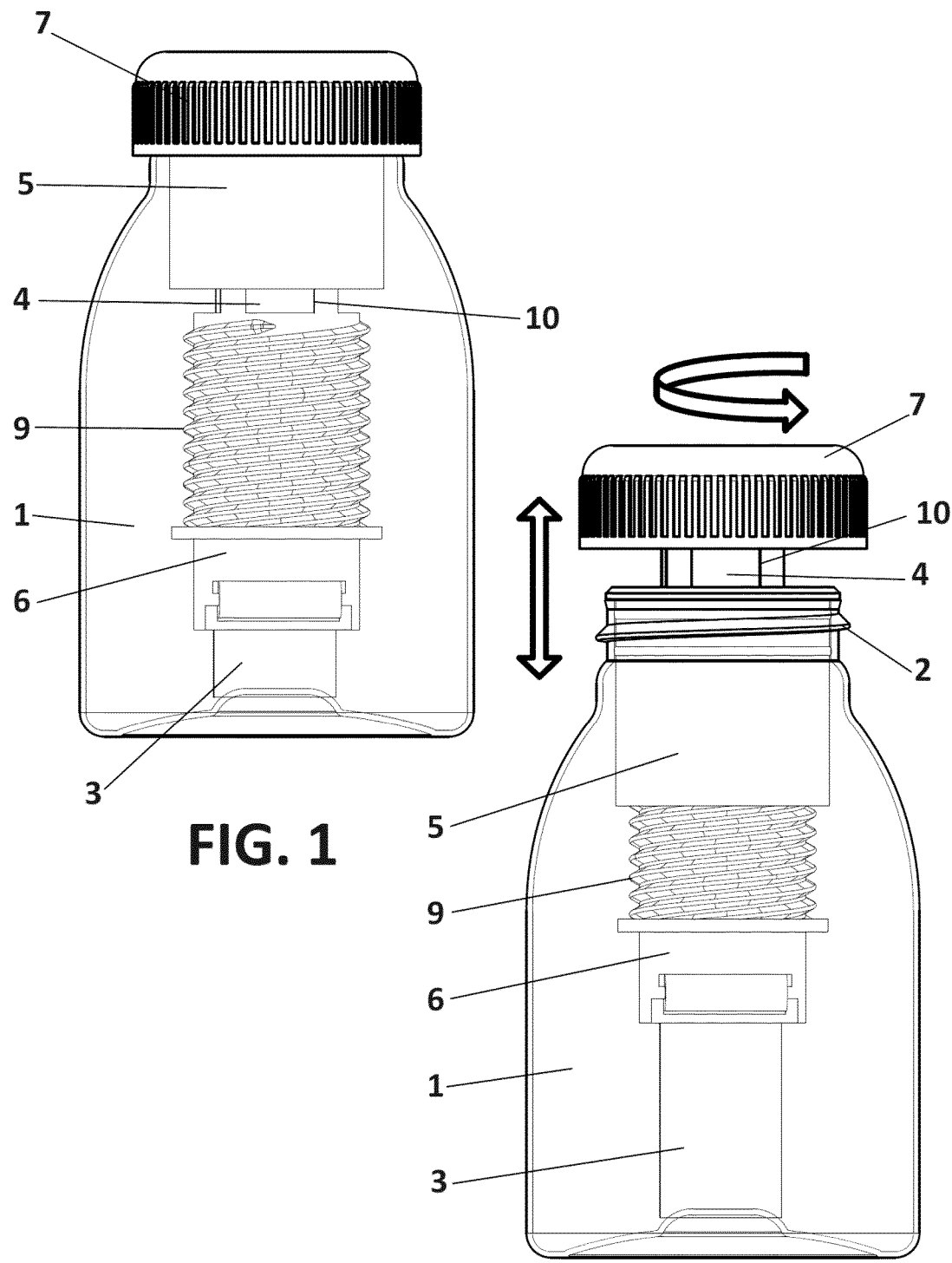

DEVICE FOR DIFFUSING VOLATILE SUBSTANCES

CROSS-REFERENCE TO RELATED APPLICATIONS

The present application is a 35 U.S.C. §§ 371 national phase patent application based on PCT/EP2017/063801, filed Jun. 7, 2017, which claims priority to Spanish Patent Application No. P201630769, filed Jun. 8, 2016, the entire contents of both applications being incorporated herein by reference. The PCT International Application was published in the English language.

The present invention relates to a device for diffusing volatile substances, for example, perfume, the diffusion of which can be adjusted by varying the evaporation surface exposed to the atmosphere.

BACKGROUND OF THE INVENTION

In the field of air fresheners and insecticides there are devices for diffusing volatile substances which enable the regulation of said diffusion by varying the evaporation surface exposed to the atmosphere.

One type of these devices comprises a flexible band of porous elements that moves by translation with respect to the neck of a bottle, where it is housed. This flexible band is impregnated with a liquid inside the bottle, which provides the volatile substances that are diffused into the atmosphere.

For example, the flexible band can be joined to the cap of the bottle, such that upon opening the bottle, the cap can be lifted to a greater or lesser extent to determine the evaporation surface exposed to the atmosphere and regulate the intensity of the perfume in a room. An example of this type of product is described in document U.S. Pat. No. 2,616,759. This device is of very simple construction and its use is attractive to consumers due to its low cost.

However, these types of products that currently exist in the market which regulate the evaporation surface through the movement of a band have the drawback of not being accurate, since they have few predefined and also not very robust positions, which implies that it is easy for the band to leave the predefined position. Thus, the user cannot accurately decide in what position to place the band and, therefore, the desired olfactory intensity.

Additionally, these devices have the additional drawback that the liquid that impregnates the band can be spilled in the event that the bottle falls accidentally or is pressed when full, since there is no element that prevents the liquid from flowing out of the bottle.

DESCRIPTION OF THE INVENTION

The device for diffusing volatile substances according to the present invention resolves the aforementioned drawbacks and has other advantages described below.

The device for diffusing volatile substances according to the present invention comprises a receptacle that defines a neck wherein a liquid that impregnates diffusion means is housed inside the receptacle, and is characterised in that:
said diffusion means comprise a flexible band and a rigid band in contact with each other, the flexible band being in contact with the liquid inside the receptacle,
the device also comprises an inner closing element that fits tightly inside said neck and a regulation element complementary to said inner closing element,
wherein the rigid band is associated with said regulation element, the position of which determines the surface of the rigid band arranged on the outside of the receptacle.

Advantageously, said regulation element is arranged around said rigid band, and said regulation element is connected to said inner closing element by means of threading.

If desired, said receptacle may also comprise a cap, which is connected to said rigid band, such that the exposed surface of the rigid band can be adjusted by means of said cap.

Additionally, the rigid band is advantageously housed inside a housing of the regulation element in a tight-fitting manner.

According to a preferred embodiment, said regulation element comprises a plurality of windows for diffusing the volatile substances.

With the device for diffusing volatile substances according to the present invention, the exposed surface of the rigid band can be accurately regulated, thereby regulating the intensity of perfume in a room.

Additionally, it prevents the liquid inside the receptacle from being accidentally spilled, since the mouth of said receptacle is hermetically sealed.

BRIEF DESCRIPTION OF THE FIGURES

In order to more readily understand the foregoing, it is accompanied by a set of drawings in which, schematically and solely by way of illustration and not limitation, a practical case of embodiment is represented.

FIG. 1 shows an elevational view of the device for diffusing volatile substances according to the present invention in its closed position.

FIG. 2 shows an elevational view of the device for diffusing volatile substances according to the present invention in its open position.

DESCRIPTION OF A PREFERRED EMBODIMENT

Figure 3:
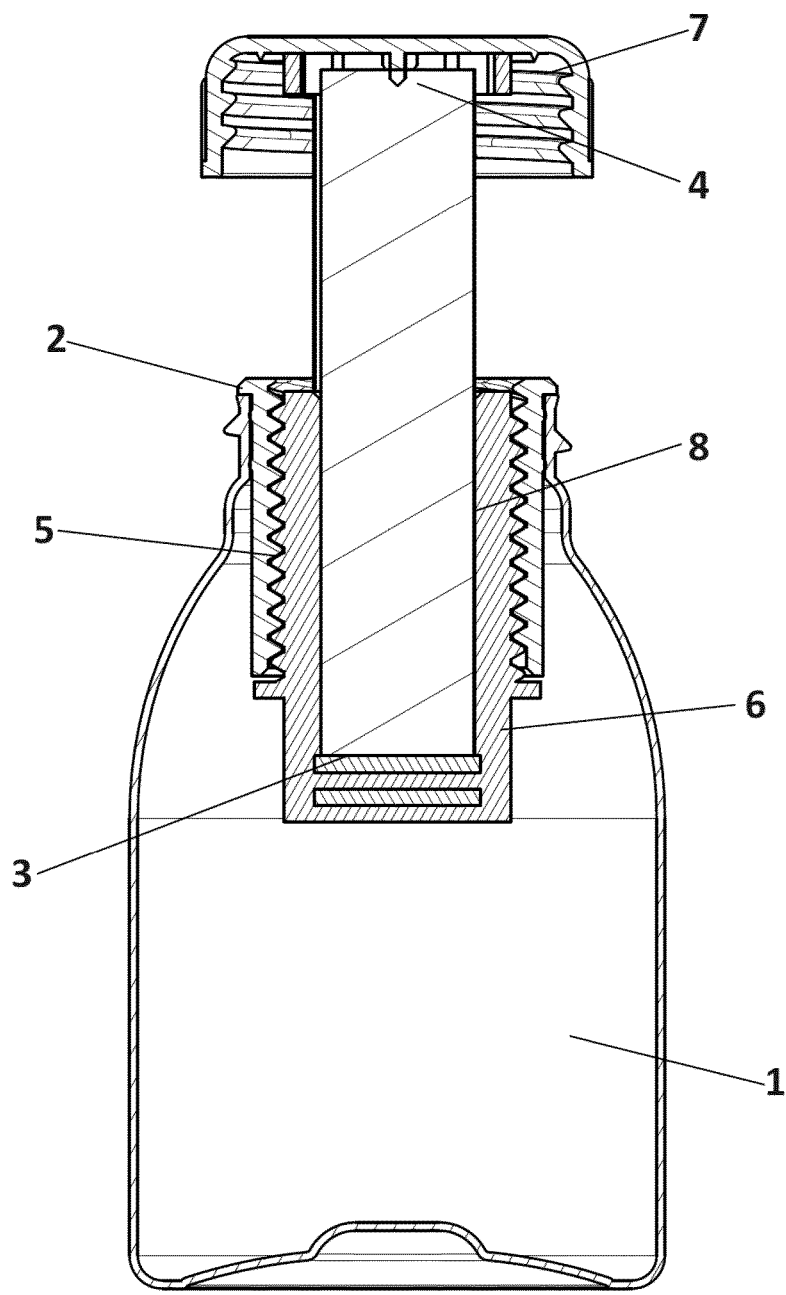
FIG. 3 shows a cross-sectional elevational view of the device for diffusing volatile substances according to the present invention in its closed position.

The device for diffusing volatile substances according to the present invention comprises a receptacle (1), for example, a bottle, inside of which a liquid is housed. Said receptacle (1) defines a neck (2) that can be closed externally by means of a cap (7).

The device according to the present invention also comprises means for diffusing volatile substances comprising a flexible band (3) and a rigid band (4) in contact with each other, such that said flexible band (3) is impregnated with the liquid inside the receptacle (1) and passes said impregnated liquid to the rigid band (4), which may be completely placed inside the receptacle (1) (closed position, FIG. 1) or outside the receptacle (1) (open position, FIG. 2) to a greater or lesser extent.

An inner closing element (5) is placed inside the receptacle (1) in contact with the neck (2) thereof, said inner closing element (5) being associated with a regulation element (6), for example, by means of threading (9), as shown in the figures.

Said regulation element (6) is moveable with respect to said inner closing element (5), for example, by means of rotation through the threading (9), as shown in the figures, or by means of translation, if the regulation element (6) were tightly fitted inside the inner closing element (5), allowing it to move.

The rigid band (4) is connected to the regulation element (6), i.e. it moves with said regulation element (6), such that the movement of the regulation element (6) will cause the rigid band (4) to be exposed to a greater or lesser extent outside the recipient (1) or be completely housed in its interior. To facilitate the diffusion of the volatile substances, the regulation element (6) may comprise a plurality of side windows (10) through which the rigid band (4) will be exposed to the atmosphere.

Said rigid band (4) is cylindrical in shape and may be placed in a tight-fitting manner (due to diameter interference) in a housing (8) of the regulation element (6), forming a watertight seal between the rigid band (4) and the regulation element (6).

Additionally, as can be observed in the figures, the flexible band (3) is joined by one of its ends, the upper end in the figures, to said regulation element (6), in contact with the rigid band (4).

If desired, the upper end of the rigid band (4) and/or the regulation element (6) may be joined to the cap 70, thereby facilitating the movement of said rigid band (4) and/or the regulation element (6).

The joint between the regulation element (6) and the cap (7) exerts pressure on the rigid band (4), ensuring physical contact and, therefore, capillarity for transmitting the liquid between the flexible band (3) and the rigid band (4).

It should be noted that the material of the flexible (3) and rigid (4) bands may be any suitable material that enables the impregnation of said bands and the diffusion of the volatile substances, for example, perfume or insecticide. Additionally, the two bands may be made of different materials.

The operation of the device according to the embodiment shown is as follows. From the closed position shown in FIG. 1, if the user wishes to use the device, the coupling of the regulation element (6) to the cap (7) can firstly be envisaged, which will be performed by turning the cap (7) while moving it slightly downwards or by direct coupling therebetween. Next, the user will unscrew the cap (7).

Once the cap (7) is unscrewed, the user will continue to turn the cap (7) such that the regulation element (6) moves vertically, causing a portion of the rigid band (4) to be exposed outside of the container (1).

Since the rigid band (4) will be impregnated with the liquid inside the receptacle (1) due to its contact with the flexible band (3), the volatile substances impregnated in the rigid band (4) will be diffused to the atmosphere.

If the receptacle (1) is accidentally tipped over, the liquid will remain inside the container (1), since the inner closing element (5) and the regulation element (6) will prevent it from spilling upon forming a watertight sealing of the receptacle (1).

To close the receptacle (1), the user simply has to move the cap (7) to its closed position by turning it in the opposite direction and screwing it on the neck (2).

In spite of the fact that reference has been made to a specific embodiment of the invention, it is evident for the person skilled in the art that the device for diffusing volatile substances described is susceptible to numerous variations and modifications, and that all the aforementioned details may be replaced by other, technically equivalent ones without detracting from the scope of protection defined by the attached claims.

The invention claimed is:

1. A device for diffusing volatile substances, the device comprising:
   a receptacle that defines a neck and is configured to hold a liquid;
   a cap configured to openably seal the receptacle;
   a diffuser comprising a first band and a second band in contact with the first band, the first and second bands being impregnated by the liquid, the first band being positioned to be in contact with the liquid inside the receptacle, the second band being made of a different material than the first band and being configured to support a weight of the cap in an open position of the receptacle,
   wherein the first band transmits the liquid by capillary action to the second band;
   an inner closing element that fits liquid sealingly inside said neck, and a regulation element cooperating with said inner closing element; and
   the second band is connected to said regulation element, and the regulation element is configured to be positionable so as to determine an amount of a surface of the second band that is arranged on an outside of the receptacle,
   wherein the first band is more flexible than the second band,
   wherein the length of the first band changes when the regulation element moves with respect to the receptacle, and
   wherein the first band remains in the receptacle in both the open and sealed positions of the receptacle.

2. The device according to claim 1, wherein said regulation element is arranged around said second band.

3. The device according to claim 1, wherein said regulation element is connected by threading to said inner closing element.

4. The device according to claim 1, wherein the cap is connected to the regulation element, synchronising its movements.

5. The device according to claim 1, wherein the second band is housed inside a housing of the regulation element so as to be liquid sealing except through diffusion through the second band.

6. The device according to claim 1, wherein the second band and the first band are housed inside the regulation element.

7. The device according to claim 3, wherein said inner closing element is integrated in the neck of the receptacle.

8. The device according to claim 5, wherein said regulation element comprises a plurality of windows for diffusing the volatile substances.

9. The device according to claim 4, wherein the cap, upon being coupled to the regulation element, exerts pressure on the second band, ensuring contact between the first band and the second band.

10. The device according to claim 5, wherein the second band is cylindrical in shape and has a diameter that is fitted to the regulation element.

11. The device according to claim 1, wherein the cap is connected to the regulation element such that in the sealed position of the cap, the cap exerts pressure on the second band to ensure contact between the first band and the second band.

12. The device according to claim 1, wherein a bottom of the first band remains at a bottom of an inside of the receptacle in both the open and sealed positions of the cap.

* * * * *